(12) United States Patent
Biedermann (10) Patent No.: US 12,343,264 B2
(45) Date of Patent: Jul. 1, 2025

(54) INTER VERTEBRAL IMPLANT AND INSERTION DEVICE THEREFOR

(71) Applicant: BIEDERMANN TECHNOLOGIES GMBH & CO. KG, Donaueschingen (DE)

(72) Inventor: Timo Biedermann, Trossingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 604 days.

(21) Appl. No.: 17/536,824

(22) Filed: Nov. 29, 2021

(65) Prior Publication Data

US 2022/0151796 A1    May 19, 2022

Related U.S. Application Data

(63) Continuation of application No. 17/020,205, filed on Sep. 14, 2020, now Pat. No. 11,241,318.
(Continued)

(30) Foreign Application Priority Data

Sep. 18, 2019  (EP) ..................... 19198123

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2/4684* (2013.01); *A61F 2002/30092* (2013.01); *A61F 2002/30985* (2013.01)

(58) Field of Classification Search
CPC ....... A61F 2/4611; A61F 2/4455; A61F 2/447
See application file for complete search history.

(56) References Cited

U.S. PATENT DOCUMENTS 8,673,012 B2    3/2014    Smith et al.
9,687,356 B1    6/2017    Spangler et al.
(Continued)

FOREIGN PATENT DOCUMENTS

CN    107320165 A    11/2017
EP    3 127 499 A1    2/2017
(Continued)

OTHER PUBLICATIONS

Extended European Search Report for Application No. 19198123.2, dated Mar. 19, 2020, 9 pages.

*Primary Examiner* — Eduardo C Robert
*Assistant Examiner* — Michelle C Green
(74) *Attorney, Agent, or Firm* — Womble Bond Dickinson (US) LLP (57) ABSTRACT

An intervertebral implant includes a body with a first face, a second face connected to the first face, and an axis of rotation. The body defines a hollow space for connecting to an insertion device, the hollow space being accessible through an opening formed between the first and second faces. The opening is elongate and extends around the axis of rotation to facilitate pivoting of the implant relative to the insertion device about the axis of rotation to a first angular position and a second angular position. The implant further includes a first abutment surface that engages the insertion device in a form-fit manner at the first angular position, and a second abutment surface that engages the insertion device in a form-fit manner at the second angular position. The opening can also engage the insertion device to hold the implant at at least one additional angular position.

22 Claims, 10 Drawing Sheets

Related U.S. Application Data (60) Provisional application No. 62/901,944, filed on Sep. 18, 2019.

(56) References Cited

U.S. PATENT DOCUMENTS

| | | | |
|---|---|---|---|
| 11,241,318 B2* | 2/2022 | Biedermann | A61F 2/4455 |
| 2005/0096745 A1* | 5/2005 | Andre | A61F 2/4611 |
| | | | 623/17.11 |
| 2006/0229627 A1* | 10/2006 | Hunt | A61F 2/4465 |
| | | | 606/86 R |
| 2007/0282441 A1 | 12/2007 | Stream et al. | |
| 2009/0265008 A1* | 10/2009 | Thibodeau | A61F 2/4611 |
| | | | 623/17.16 |
| 2010/0256759 A1 | 10/2010 | Hansell et al. | |
| 2011/0264218 A1* | 10/2011 | Asaad | A61F 2/30767 |
| | | | 623/17.16 |
| 2011/0276142 A1 | 11/2011 | Niemiec et al. | |
| 2012/0165943 A1 | 6/2012 | Mangione et al. | |
| 2012/0209383 A1* | 8/2012 | Tsuang | A61F 2/46 |
| | | | 623/17.12 |
| 2013/0023937 A1 | 1/2013 | Biedermann et al. | |
| 2016/0317320 A1 | 11/2016 | Ahn | |
| 2017/0056194 A1* | 3/2017 | Biedermann | A61F 2/4611 |
| 2017/0172759 A1* | 6/2017 | Kukkar | A61F 2/4465 |

FOREIGN PATENT DOCUMENTS

| | | |
|---|---|---|
| EP | 3 135 254 A1 | 3/2017 |
| FR | 2 948 277 A1 | 1/2011 |
| JP | 2013-000595 A | 1/2013 |

\* cited by examiner

INTER VERTEBRAL IMPLANT AND INSERTION DEVICE THEREFOR

CROSS-REFERENCE TO RELATED APPLICATION(S)

This application is a continuation of U.S. patent application Ser. No. 17/020,205, filed Sep. 14, 2020, which claims priority to and the benefit of U.S. Provisional Patent Application No. 62/901,944, filed Sep. 18, 2019, the contents of which are hereby incorporated by reference in their entirety, and claims priority from European Patent Application EP 19 198 123.2, filed Sep. 18, 2019, the contents of which are hereby incorporated by reference in their entirety.

BACKGROUND

Field

The application relates to an intervertebral implant and an insertion device for such an intervertebral implant. The intervertebral implant and the insertion device may be used, for example, for spinal fusion in cases involving a damaged intervertebral disk.

Description of Related Art

Lumbar or thoracic interbody fusion surgery is one of the most commonly performed spinal fusion surgeries using an instrument. Some known surgical approaches for interbody fusion of the lumbar spine include posterior lumbar interbody fusion (PLIF), transforaminal lumbar interbody fusion (TLIF), anterior lumbar interbody fusion (ALIF), anterolateral ALIF, and lateral interbody fusion.

An intervertebral implant and a device for inserting the same that are, for example, suitable for TLIF are described in US 2017/0056194 A1. The intervertebral implant has a top surface, a bottom surface, a sidewall extending between the top surface and the bottom surface, and a hollow space formed within the intervertebral implant and accessible through an elongate opening extending through a recessed portion of the sidewall. The hollow space is shaped to receive an engagement portion of a drive shaft of an insertion tool. The intervertebral implant includes at least two guiding surfaces facing each other and configured for sliding engagement by a portion of a sleeve of the insertion tool that movably holds the drive shaft.

SUMMARY

It is an object of the invention to provide an improved or alternative intervertebral implant and an insertion device that has an increased field of application.

The intervertebral implant is designed to permit pivoting of the insertion device relative to the intervertebral implant and locking of the intervertebral implant relative to the insertion device at at least two pivot positions, for example, by a form-fit connection. Such a form-fit connection is more robust compared to a force-fit connection that is based on friction. This enhances safety during insertion of the intervertebral implant, where often large forces are needed.

Moreover, it is possible to insert the intervertebral implant with the insertion device at a fixed position defined by the form-fit connection and, if necessary, to adjust the position of the implant after releasing the form-fit connection, and/or to pivot the implant relative to the insertion device while the implant is still safely connected thereto. By means of such a procedure, corrections of the position of the implant can be made.

According to a further embodiment, the intervertebral implant may have more than two different surfaces for defining different pivot angles for a form-fit connection between the intervertebral implant and the insertion device. Therefore, with a single intervertebral implant, different access paths to the intervertebral space may be possible and different surgical techniques can be implemented. Hence the field of application of the intervertebral implant can be further increased.

According to a still further embodiment, the intervertebral implant may have at least one guiding surface for pivoting of the intervertebral implant and the insertion device relative to each other along the guiding surface, and for frictional clamping of the implant and the insertion device with respect to each other at a particular position along the cooperating guiding surfaces.

According to a still further embodiment, the intervertebral implant may include further receiving sections for receiving the insertion device in a non-pivotable manner at other locations on the implant.

According to a still further embodiment, the intervertebral implant can be a dummy implant or testing implant that is used for a trial procedure, before inserting a permanent intervertebral implant in a patient's body.

Thus, the intervertebral implant can be used, for example, for various surgical procedures, such as TLIF, ALIF, anterolateral ALIF, PLIF, and lateral interbody fusion, but is not restricted thereto, using the same intervertebral implant and insertion device. Due to the increased possibilities of connecting the implant to the insertion device, the implant may be particularly useful in cases with difficult anatomical circumstances, such as in anterior and lateral approaches to the spine.

BRIEF DESCRIPTION OF THE DRAWINGS

Further features and advantages will become apparent from the detailed description of embodiment by means of the accompanying drawings. In the drawings.

DETAILED DESCRIPTION

Figure 1:
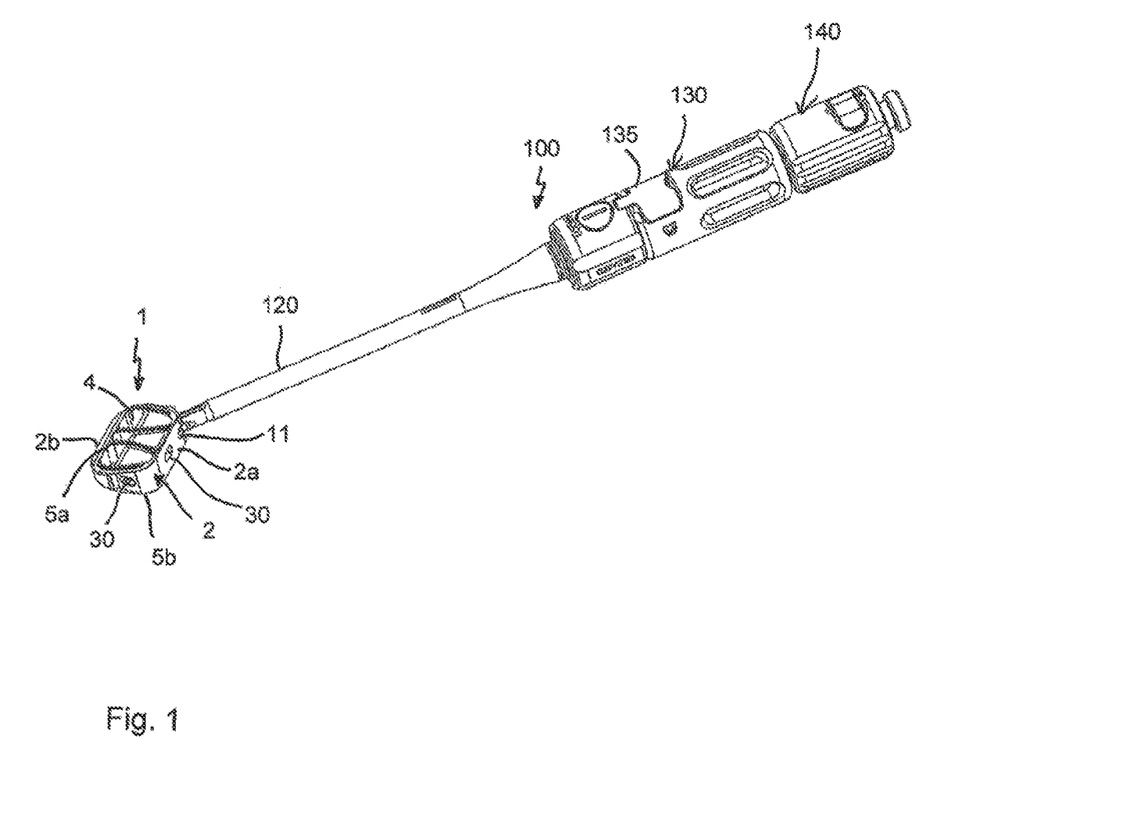
FIG. 1 shows a perspective view of a system including an intervertebral implant according to a first embodiment with an insertion device connected thereto.

FIG. 1 shows a perspective view of an intervertebral implant and an insertion device 100 for inserting the intervertebral implant 1 into an intervertebral space. The intervertebral implant 1 has a body including a substantially vertical sidewall 2 defining a height of the intervertebral implant 1. The sidewall 2 is formed monolithically with an inner solid portion 3 and encloses one or more inner hollow spaces 4. The hollow spaces 4 are open towards an upper face 5a and a lower face 5b of the intervertebral implant 1.

In greater detail, the sidewall 2 is formed by a front wall 2a, an opposite back wall 2b, a right sidewall 2c, and a left sidewall 2d, which are monolithically formed, such that the right and left sidewalls connect the front wall 2a and the back wall 2b with each other. The front wall 2a represents an anterior wall and the back wall 2b represents a posterior wall of the intervertebral implant 1. The front wall 2a and the back wall 2b may be longer than the right sidewall 2c and the left sidewall 2d, so that the intervertebral implant has an elongate outer contour. In the embodiment shown, the front wall 2a and the back wall 2b are substantially parallel to each other and define a longitudinal central axis LI of the intervertebral implant (indicated in FIG. 11a). Optionally, inner walls 6a, 6b may extend in an arc-shaped manner from the front wall 2a to the back wall 2b. Both inner walls 6a, 6b may be symmetric with respect to a sagittal plane S (indicated in FIG. 11a) that extends vertically through centers of the front wall 2a and the back wall 2b. The solid portion 3 extends from the front wall 2a to a distance from the back wall 2b, and has a length such that receiving portions in the form of recesses, as further described below, can be formed in the solid body 3 with depths sufficient for engagement with the insertion device 100. The sidewall 2 may have such a height that the top surface 5a and the bottom surface 5b extend above the solid portion 3.

The hollow spaces 4 are configured to be filled with bone graft material. Further, engagement portions, for example, teeth 7, may be provided on the upper face 5a and the lower face 5b of the intervertebral implant, which may facilitate penetration into the end plates of adjacent vertebral bodies. The front wall 2a and the back wall 2b may have different heights, such that the top face 5a and the bottom face 5b form an angle, resulting in the intervertebral implant 1 having a wedge shape.

Figure 2:
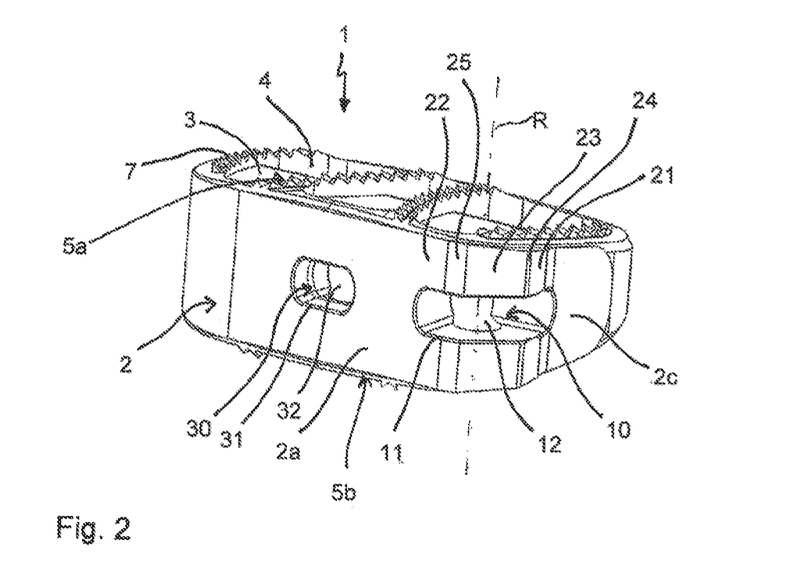
FIG. 2 shows a perspective view of the intervertebral implant of FIG. 1 from one side, showing an elongate opening for connection with the insertion device.

As can be seen in detail in particular in FIG. 2, at the transition of the front wall 2a to the right sidewall 2c, a recess 10 is provided that forms an elongate opening 11 in the sidewall 2. The recess 10 defines a hollow space within the intervertebral implant 1 for receiving a portion of the insertion device. The recess 10 extends into the solid portion 3 and forms a corner with an angle of substantially 90° degrees therein. Thereby, left and right end walls of the recess 10 form an angle of substantially 90°. The recess 10 and the opening 11 may be provided at a middle of the sidewall 2 in the height direction.

A width of the recess 10 in the height direction is such that an engagement portion of the insertion device can be introduced in one orientation but cannot be introduced in a tilted orientation. Top and bottom walls of the recess 10 may be planar, and may extend substantially parallel to each other and substantially perpendicular to the sidewall 2. The opening 11 extends in a circumferential direction from the front wall 2a over a corner between the front wall 2a and the right sidewall 2c into the right sidewall 2c. Hence, the elongate opening 11 and the recess 10 have a size such that a drive shaft of the insertion device can assume an angle as small as about 0° and an angle as large as about 90° with the central longitudinal axis LI of the intervertebral implant 1.

In the inside corner of the recess 10, a spherically-shaped recess 12 is formed that is configured to pivotably receive the engagement portion of the insertion device 100. A radius of the spherically-shaped recess 12 matches a radius of an outer surface of the engagement portion of the drive shaft. The spherical recess 12 is sized to permit the engagement portion of the insertion device to pivot therein in an angular range of about 90° or more. An axis R extending through a center of the spherically-shaped recess 12 and parallel to the sidewall 2 forms an axis of rotation, and more specifically a pivot axis for pivotal movement between the intervertebral implant 1 and the insertion device 100.

The sidewall 2 has, in the region of the elongate opening 11, outer surfaces that are shaped to provide abutment surfaces for the insertion device to achieve a form-fit engagement and/or to provide guiding surfaces for pivotal movement of the insertion device. As can be seen in greater detail in FIG. 11a, the sidewall 2 protrudes outward in the region of the recess 10 in an substantially polygonal contour due to the presence of the abutment surfaces.

Figure 3:
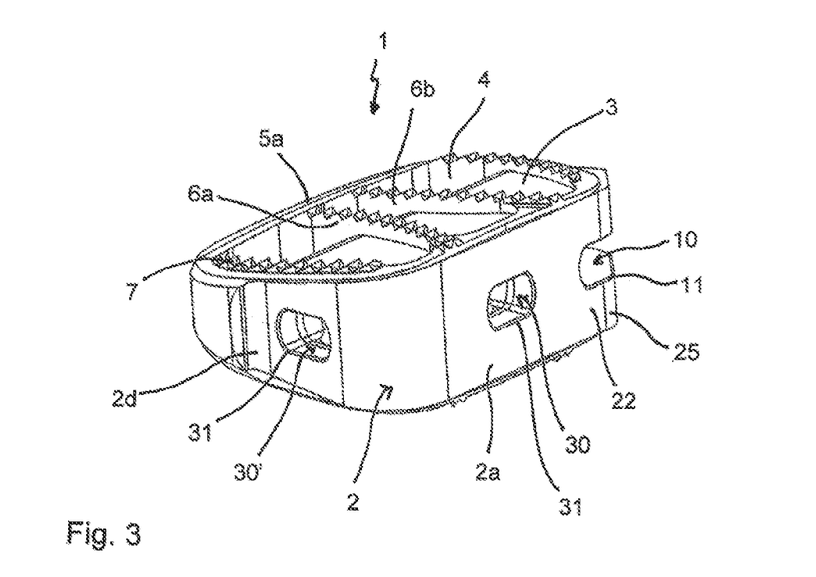
FIG. 3 shows a perspective view of the intervertebral implant of FIGS. 1 and 2 from another side, showing a further opening for connection with the insertion device.
Figure 11A:
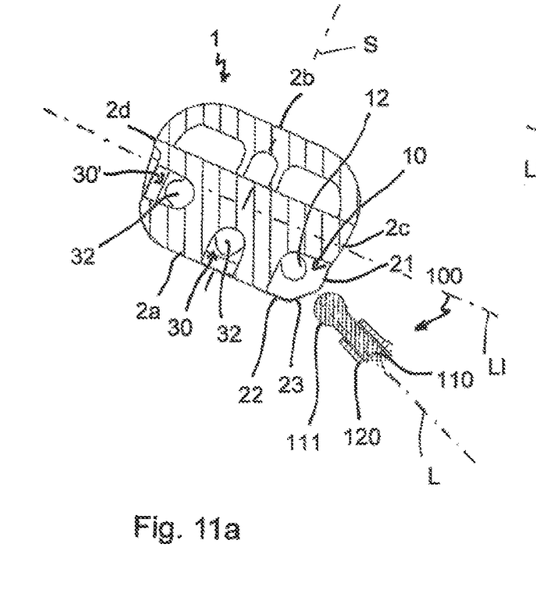
FIGS. 11a to 11d show cross-sectional views of steps for connecting a front portion of the insertion device to the intervertebral implant, wherein the cross-section is taken in a plane extending through the intervertebral implant and including a longitudinal axis of the insertion device.

Referring in particular to FIGS. 2, 3 and 11a, a first abutment surface 21 is provided around the lateral edge of the elongate opening 11 that extends into the right sidewall 2c. The first abutment surface 21 is substantially planar and is configured to provide a form-fit engagement with the insertion device when an angle of 0° is formed between a central longitudinal axis L of the insertion device (see FIGS. 4 to 8) and the central longitudinal axis LI of the intervertebral implant. A second abutment surface 22 is provided around the opposite lateral edge of the elongate opening 11 that extends into the front wall 2a. The second abutment surface 22 is substantially planar and is configured to provide a form-fit engagement with the insertion device when an angle of 90° is formed between the central longitudinal axis L of the insertion device and the central longitudinal axis LI of the intervertebral implant 1. A third abutment surface 23 extends around substantially a center of the opening 11 and forms an angle of 45° with the first abutment surface 21 and the second abutment surface 22. Hence, the third abutment surface 23 is configured to provide a form-fit engagement with the insertion device when an angle of 45° is formed between the central longitudinal axis L of the insertion device and the central longitudinal axis LI of the intervertebral implant 1.

The sidewall 2 further includes a first guiding surface 24 that is provided between the first abutment surface 21 and the third abutment surface 23, and that is cylindrical with a cylinder axis being coaxial with the rotational axis R. A second guiding surface 25 is provided between the second abutment surface 22 and the third abutment surface 23, and is also cylindrical with a cylinder axis that is coaxial with the rotational axis R. The first and second guiding surfaces 24, 25 allow a guided rotational, and more particularly a pivotal, movement between the intervertebral implant 1 and the insertion device 100 when the insertion device is connected and, for example, slightly frictionally clamped to the intervertebral implant 1.

Optionally the intervertebral implant 1 may include further receiving portions, for example, recesses in the sidewall 2 for connection with the insertion device 100 to permit the placement of the intervertebral implant with the insertion device using various other surgical approaches. In the embodiment shown, the intervertebral implant has an additional recess 30 at substantially the center of the front wall 2a and an additional recess 30' at the left sidewall 2d.

Figure 11B:
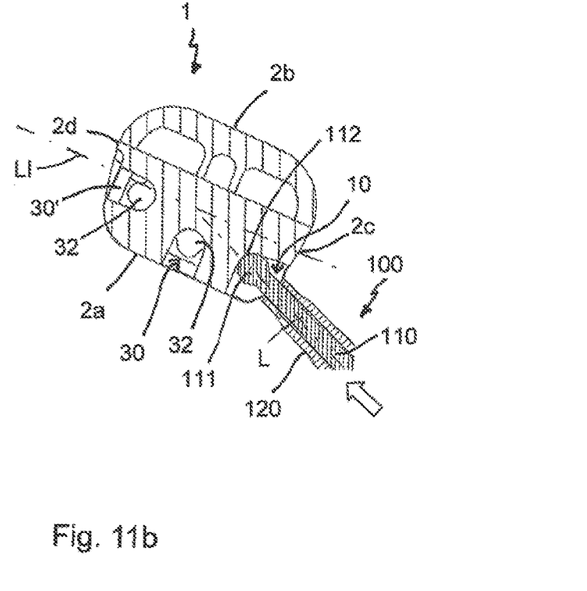

The recesses 30, 30' each have an overall inner cross-section that corresponds to a circle, with cut away opposite sides so as to provide an elongate opening 31 with flat upper and lower edges that are parallel to the upper and lower edges of the sidewall 2. The size of the recesses 30, 30' is such that the engagement portion of the drive shaft can be inserted in one orientation, but cannot be inserted in a tilted orientation. As shown in greater detail, for example, in FIGS. 11a to 11c, each recess 30, 30' has an inner spherically-shaped recess 32, the radius of which matches the radius of the engagement portion of the drive shaft, so that the engagement portion can be rotated therein to assume a 90° tilted orientation.

Turning now to FIGS. 1 to 8, the insertion device 100 will be described. The insertion device 100 includes a drive shaft 110, a guiding sleeve 120 that receives the drive shaft 110 therein, a handle 130, a rotation actuating button 135, and an axial position adjusting device 140. The drive shaft 110 is movably guided within the guiding sleeve 120 and may be advanced or retracted with respect to the guiding sleeve 120 by actuating the axial position adjusting device 140. Further, the drive shaft 110 may be rotated by actuating the rotation actuating button 135. It shall be noted that axial displacement of the drive shaft and rotation of the drive shaft may be achieved in various other ways.

Figure 4:
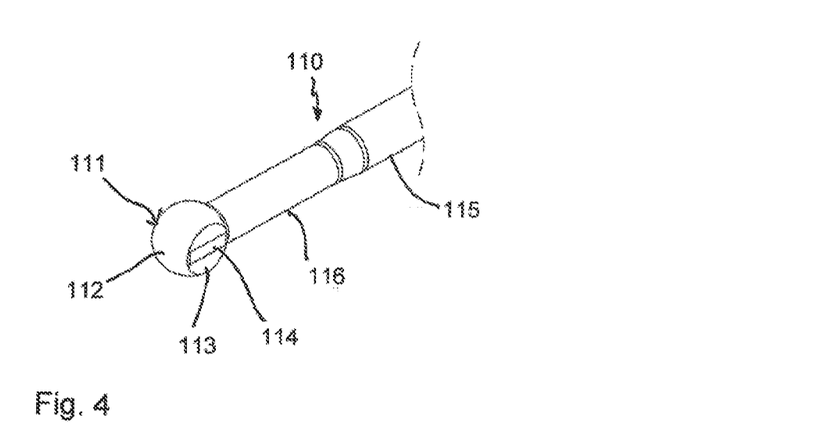
FIG. 4 shows a perspective view of a front portion of a drive shaft of the insertion device of FIG. 1.
Figure 5:
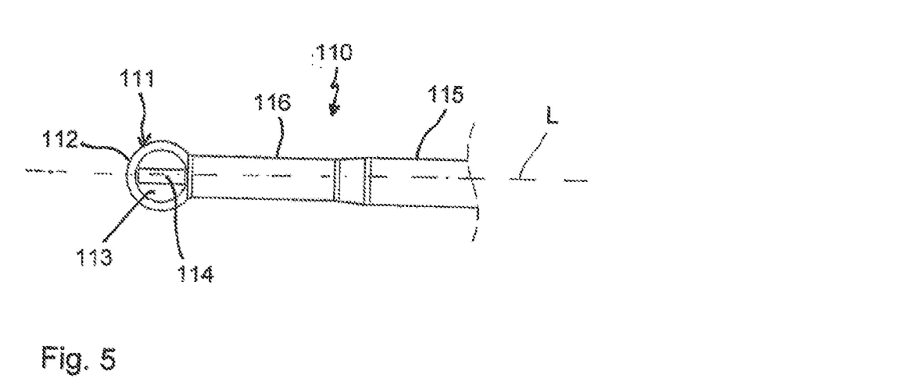
FIG. 5 shows a side view of the front portion of the drive shaft of FIG. 4.
Figure 6:
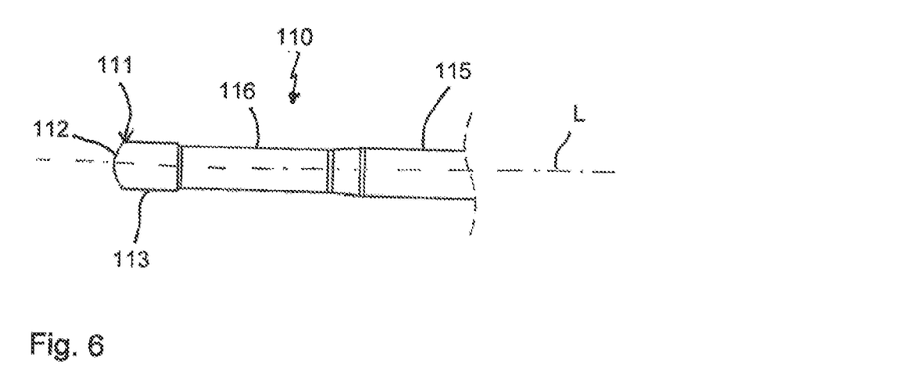
FIG. 6 shows a side view of the front portion of the drive shaft of FIG. 5 rotated by 90°.

The drive shaft 110 defines a longitudinal axis L of the insertion device, and has a front portion which is shown in greater detail in FIGS. 4 to 6. The front portion includes an engagement portion 111 with a spherical surface 112 that has the shape of a segment of a sphere. The spherical surface 112 may be formed by removing opposite segments of the sphere to yield opposite flat surfaces 113. Hence, the engagement portion 111 has a flattened shape with a thickness between the flat surfaces 113 that is slightly smaller than a vertical height of the elongate opening 11 and heights of the openings 31 of the optional recesses 30, 30'. This permits insertion of the engagement portion 111 into the recess 10 and optionally into the recesses 30, 30' of the intervertebral implant 1, in an orientation where the flat surfaces 113 extend perpendicular to the height direction of the sidewall 2.

On at least one, and preferably on both, of the flat surfaces 113, a longitudinally extending positioning mark 114 is provided, that extends parallel to the central longitudinal axis L of the insertion device.

The engagement portion 111 is connected to a main portion 115 via a neck portion 116. The neck portion 116 has an outer diameter that is smaller than the maximum diameter of the spherical surface portion 112 of the engagement portion 111. The main portion 115 may have a greater diameter than the neck portion 116. The spherical segment-shaped portion 112 of the engagement portion 111 has a size such that, once portion 112 has been inserted into the recess 10 and engages the spherical recess 12 or into one of the recesses 30, 30' and engages a spherical recess 32, portion 112 can be tilted by 90° so that the engagement portion 111 is held in but can still pivot in the spherical recess 12 or in one of the spherical recesses 32.

Figure 7:
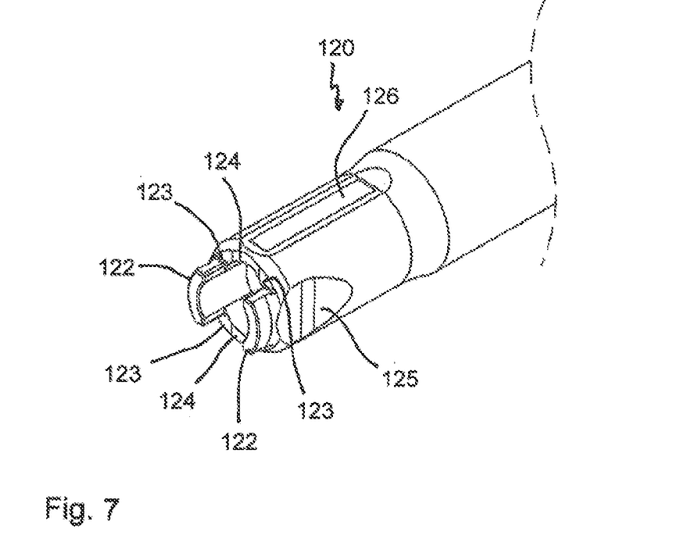
FIG. 7 shows a perspective view of a front portion of a guiding sleeve of the insertion device of FIG. 1.
Figure 8:
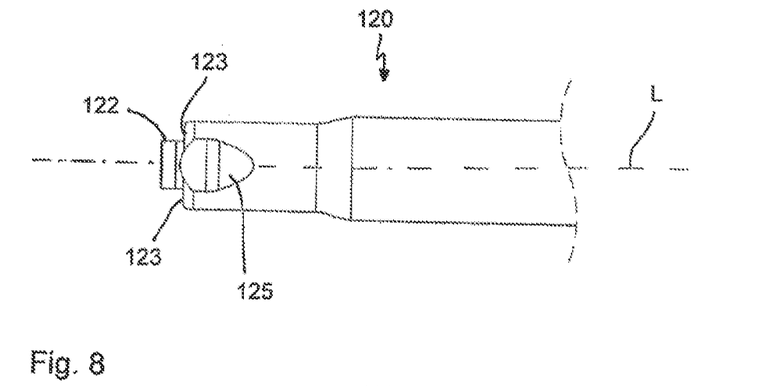
FIG. 8 shows a side view of the front portion of the guiding sleeve of FIG. 7.
Figure 9:
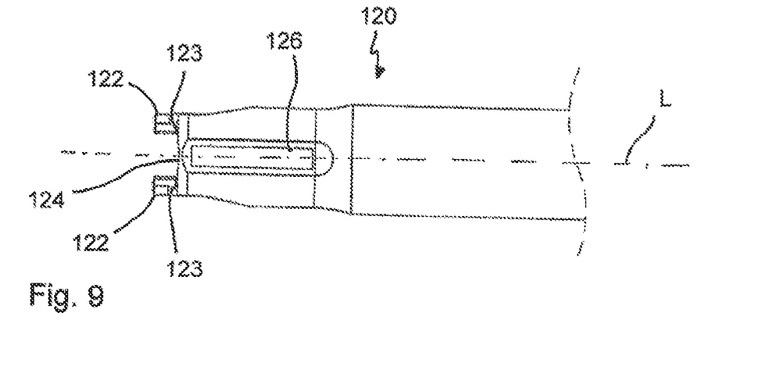
FIG. 9 shows a side view of the front portion of the guiding sleeve of FIG. 8 rotated by 90°.

The front portion of the guiding sleeve 120 is shown in greater detail in FIGS. 7 to 9. When the drive shaft 110 is arranged in the guiding sleeve 120, the engagement portion 111 protrudes out of the front portion of the guiding sleeve 120. Two opposite cylindrical projections 122 form the outermost end of the guiding sleeve 120. The cylindrical projections 122 have a size such that they are insertable into the recesses 10, 30, 30', respectively. An end face of the tubular guiding sleeve 120 includes a planar surface 123 and a concave, and more specifically a cylindrical surface 124 that is arranged between the two projections 122 and that has a cylinder axis which is perpendicular to the central longitudinal axis L. The planar surface 123 thus forms adjacent each projection 122 an abutment surface for abutting against the first or the second or the third abutment surfaces at the sidewall 2 of the intervertebral implant 1 when the guiding sleeve 120 is pressed against the sidewall 2. The cylindrical surface 124 forms a guiding surface that is configured to cooperate with the first or the second guiding surfaces 24, 25 at the sidewall 2 of the intervertebral implant to permit a guided rotational movement of the intervertebral implant relative to the insertion device. Hence, a radius of the cylindrical guiding surface 124 corresponds to a radius of the cylindrical guiding surfaces 24, 25 on the sidewall of the intervertebral implant 1.

At an outer wall of the guiding sleeve 120 adjacent to the cylindrical projections 122 in a longitudinal direction, two opposite positioning flat surfaces 125 may be provided.

The positioning flat surfaces 125 indicate the position of the cylindrical projections 122, and may serve for orienting the insertion device correctly during connection with the intervertebral implant. Moreover, at least one longitudinally extending positioning mark 126 at an outside of the front portion of the guiding sleeve 120 may further be provided that is 90° offset from the positioning flat surfaces 125 and that indicates the position of the cylindrical guiding surface 124.

When the drive shaft 110 is inserted into the guiding sleeve 120 and the engagement portion 111 projects out of the front portion of the guiding sleeve 120, the drive shaft 110 may be pushed forward and retracted by actuating the axial position adjustment device 140. The size of the projections 122 is such that the engagement portion 111 can only be retracted between the projections 122 in a 90° upright position of the engagement portion 111.

The intervertebral implant 1 may, for example, be made of titanium or stainless steel or of any bio-compatible metal or metal alloy or plastic material. With respect to bio-compatible alloys, a NiTi alloy, for example Nitinol, may be used. Other materials that can be used are, for example, magnesium or magnesium alloys. Bio-compatible plastic materials that can be used may be, for example, polyether ether ketone (PEEK) or poly-L-lactide acid (PLLA). Also the insertion device may be made of the same material as the intervertebral implant or of another material.

Figure 10A:
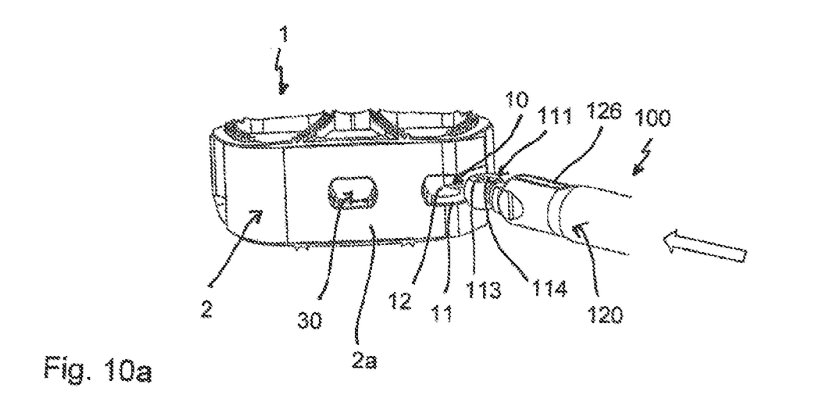
FIGS. 10a to 10c show perspective views of steps for connecting the front portion of the drive shaft of the insertion device of FIGS. 4 to 6 to the intervertebral implant of FIGS. 1 to 3.
Figure 10B:
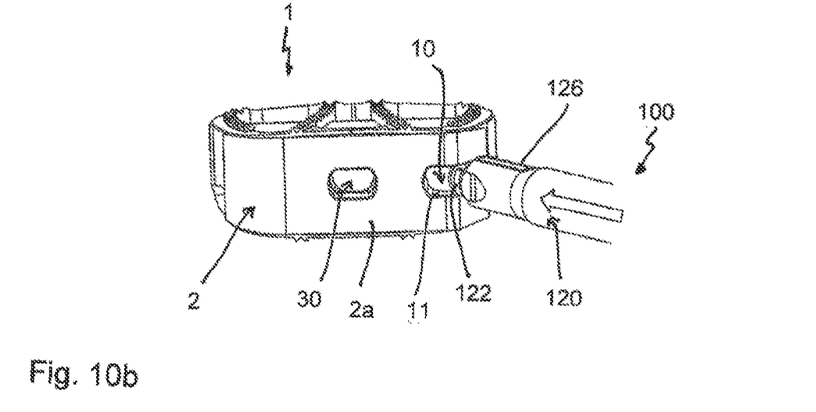

Next, the operation of the intervertebral implant 1 and the insertion device will be explained. First, steps of connecting the insertion device 100 to the intervertebral implant 1 will be explained, with reference to FIGS. 10a to 11d. As shown in FIGS. 10a and 11a, the engagement portion 111 of the drive shaft 110 protrudes out of the front portion of the guiding sleeve 120. The engagement portion 111 is oriented relative to the intervertebral implant in a manner such that the flat surfaces 113 are parallel to the upper and lower edges of the elongate opening 11. Such an orientation can be easily identified, for example, when the positioning mark 114 is aligned with the position mark 126 on the guiding sleeve 120. As further depicted in FIGS. 10b and 11b, the engagement portion 111 is inserted through the elongate opening 11 into the recess 10 until the spherical surface portion 112 abuts against the corner of the recess 10. The cylindrical projections 122 of the guiding sleeve 120 enter into the recess 10, so that the sidewall 2 can abut against the abutment surface 123 at the front portion of the guiding sleeve 120. In the insertion position shown in FIGS. 10b and 11b, the third abutment surface 23 of the intervertebral implant comes in contact with the abutment surface 123 of the guiding sleeve 120. Hence, the longitudinal axis L of the insertion device forms an angle of 45° with the central longitudinal axis LI of the intervertebral implant 1.

Figure 10C:
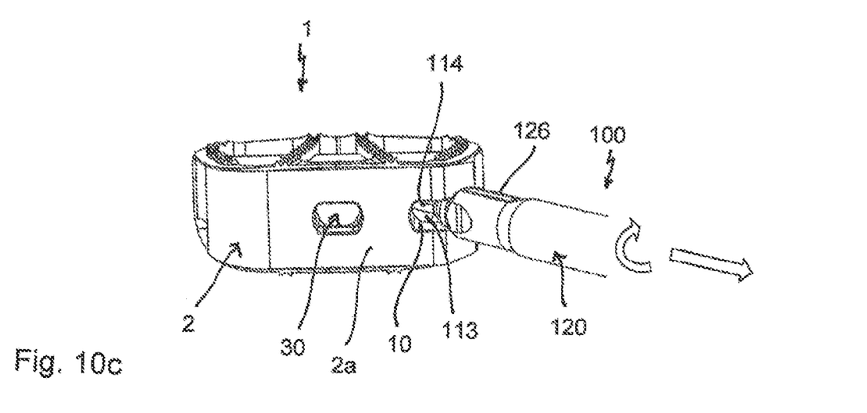
Figure 11C:
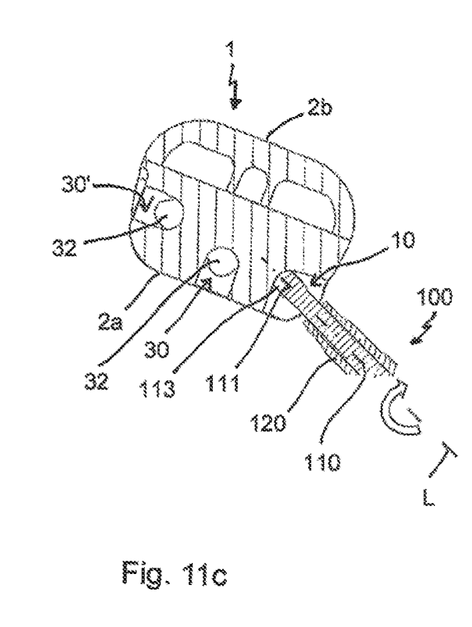

Next, as explained in FIGS. 10c and 11c, the drive shaft 110 is rotated, or tilted, in the spherical recess 12 in the intervertebral implant 1, such that the flat surfaces 113 extend vertically in the intervertebral implant. In this orientation, the spherical portion 112 of the engagement portion can pivot in the spherical recess 12 of the intervertebral implant 1. This rotation by 90° may be effected by actuating the button 135 at the handle.

Figure 11D:
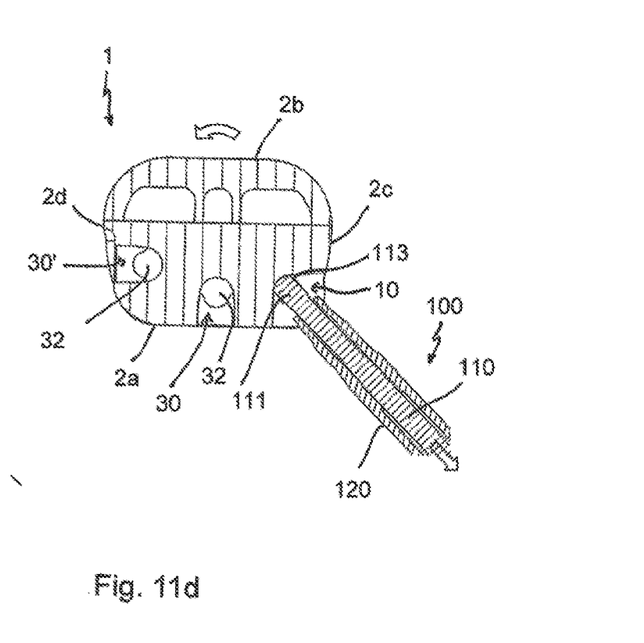

Finally, as indicated by the straight arrow in FIG. 11d, the drive shaft 110 is pulled backwards. Thereby, the drive shaft 110 can move at least partially between the cylindrical projections 122, which in turn enter further into the recess 10. When the engagement portion 111 is oriented vertically in the recess 10 and in the spherical recess 12, i.e., when the flat surfaces 113 extend parallel to the axis of rotation, the engagement portion 111 cannot be removed from the recess 10 through the opening 11. Also, if the engagement portion 111 is oriented vertically in the recesses 30, 30', the engagement portion also cannot be removed through the openings 31, respectively. At the same time the abutment surface 23 of the intervertebral implant and the abutment surface 123 of the guiding sleeve 120 are pressed against each other when the insertion device is tightened against the intervertebral implant. Due to the flat abutting surfaces, a form-fit connection is provided so that rotation, or more specifically pivoting, of the intervertebral implant relative to the insertion device is prevented. By final tightening of the insertion device relative to the intervertebral implant, the connection is locked.

Figure 12:
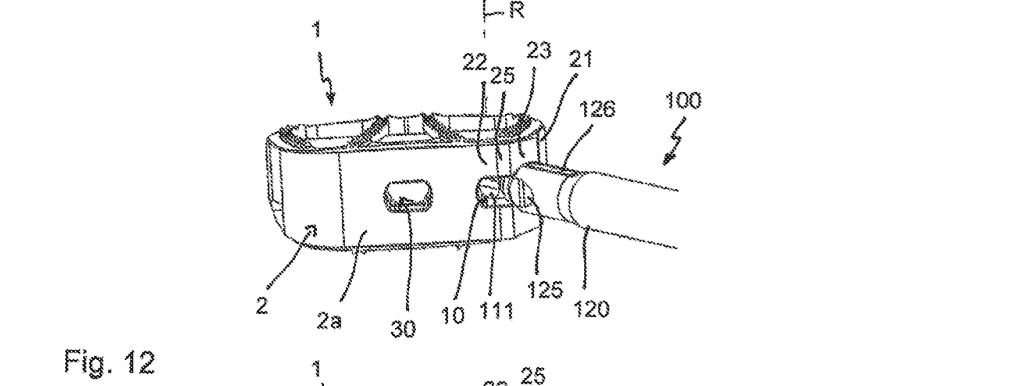
FIG. 12 shows a perspective view of a form-fit connection between the intervertebral implant and the insertion device, wherein the insertion device forms an angle of substantially 45° with a longitudinal axis of the intervertebral implant.
Figure 13:
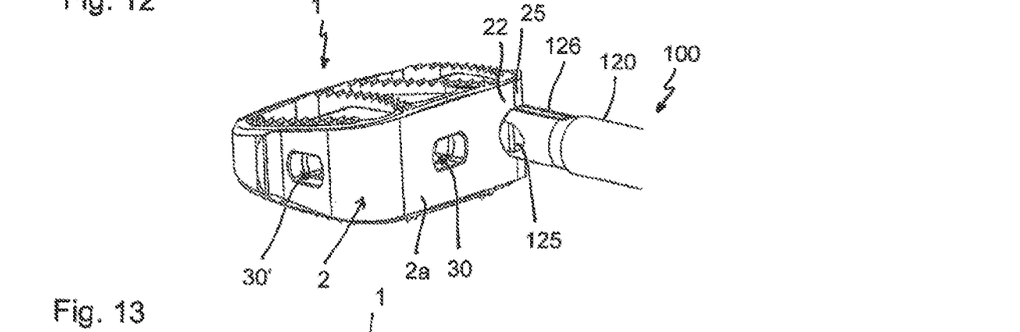
FIG. 13 shows a perspective view of a form-fit connection between the intervertebral implant and the insertion device, wherein the insertion device forms an angle of substantially 90° with the longitudinal axis of the intervertebral implant.
Figure 14:
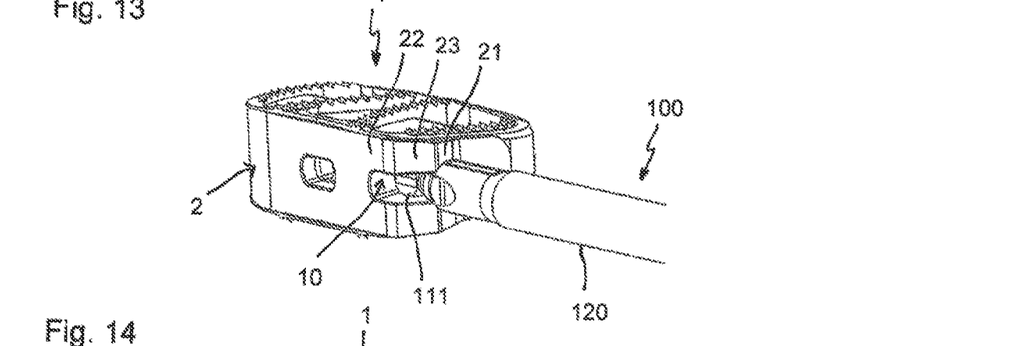
FIG. 14 shows a perspective view of a form-fit connection between the intervertebral implant and the insertion device, wherein the insertion device forms an angle of substantially 0° with the longitudinal axis of the intervertebral implant.
Figure 15:
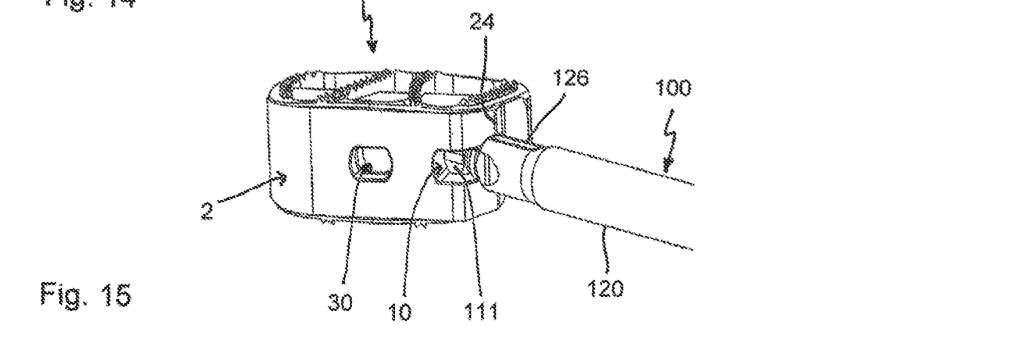
FIG. 15 shows a perspective view of a connection between the intervertebral implant and the insertion device, wherein the insertion device is at a position relative to the intervertebral implant that permits rotating and clamping of the intervertebral implant by friction.
Figure 16:
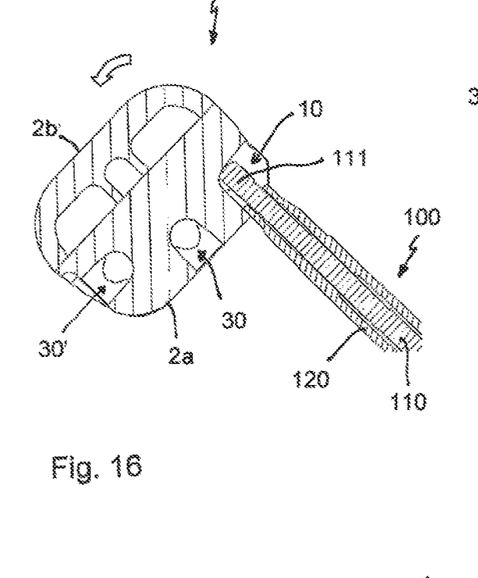
FIG. 16 shows a cross-sectional view of the connection between the intervertebral implant and the insertion device forming an angle of substantially 90°, for example, as shown in FIG. 13.
Figure 17:
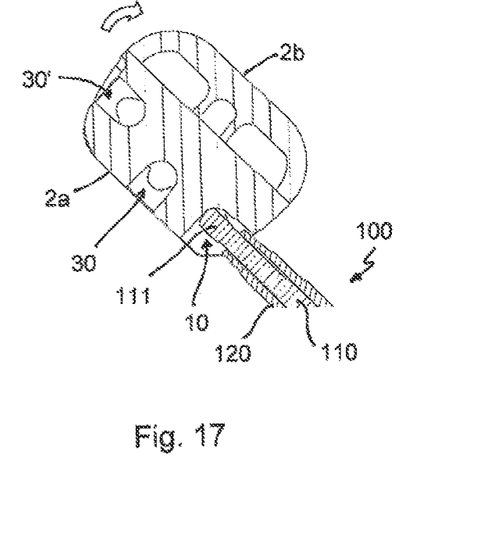
FIG. 17 shows a cross-sectional view of the connection between the intervertebral implant and the insertion device forming an angle of substantially 0°, for example, as shown in FIG. 14.
Figure 18:
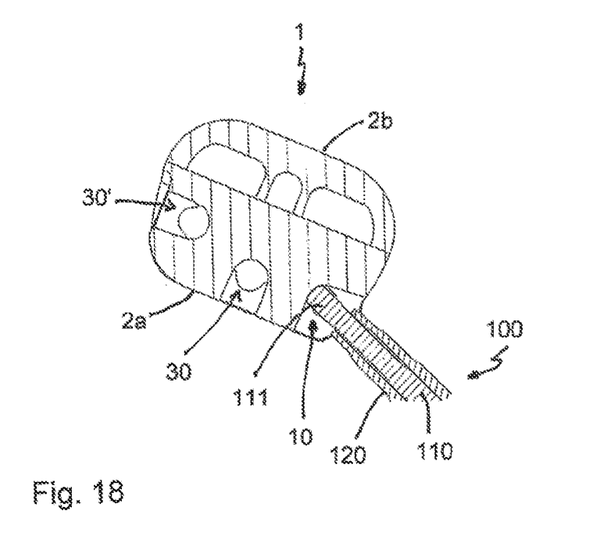
FIG. 18 shows a cross-sectional view of the connection between the intervertebral implant and the insertion device that permits adjustments to various intermediate positions, and frictional clamping of the implant and the insertion device at intermediate positions, for example, as shown in FIG. 15.

FIGS. 12 to 18 show the different orientations that the insertion device can assume with respect to the intervertebral implant 1. In FIG. 12, the third abutment surface 23 cooperates with the planar abutment surface 123 provided on the guiding sleeve 120. In this position, the insertion device and the intervertebral implant form an angle of 45°. In FIGS. 13 and 16, the intervertebral implant abuts with the second abutment surface 22 against the corresponding abutment surface 123 at the guiding sleeve 120. In this position, the insertion device and the intervertebral implant form an angle of 90°. In FIGS. 14 and 17 the intervertebral implant abuts with the first abutment surface 21 against the corresponding abutment surface 123 at the guiding sleeve 120. In this position, the insertion device and the intervertebral implant form an angle of 0°. In FIGS. 15 and 18, the intervertebral implant abuts with its cylindrical guiding surface 124 against the cylindrical guiding surface 24 at the insertion device. As the surfaces permit pivoting of the implant relative to the insertion device, there may be a frictional engagement which allows the insertion device to assume and be held at various angular positions relative to the implant. Each position can be fixed by retracting the drive shaft 110, so that the engaging surfaces are pressed more tightly against each other. In this manner, the connection can also be fixed by frictional clamping.

Figure 19:
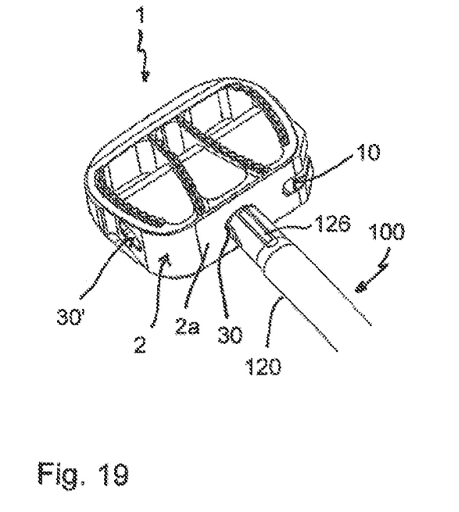
FIG. 19 shows a perspective view of the intervertebral implant with the insertion device connected to a further receiving portion.
Figure 20:
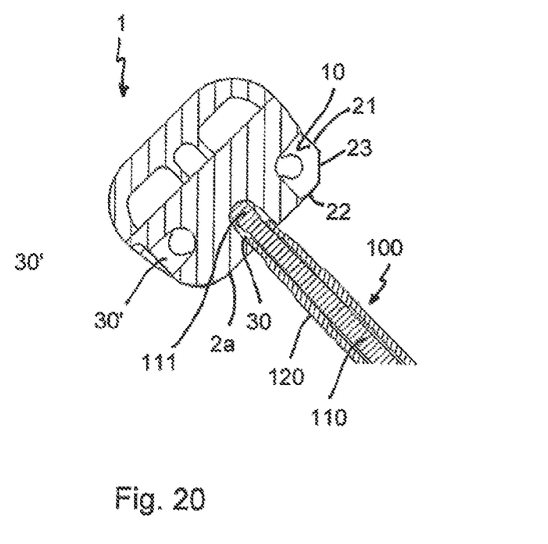
FIG. 20 shows a cross-sectional view of the intervertebral implant with the insertion device connected to the further receiving portion as shown in FIG. 19.
Figure 21:
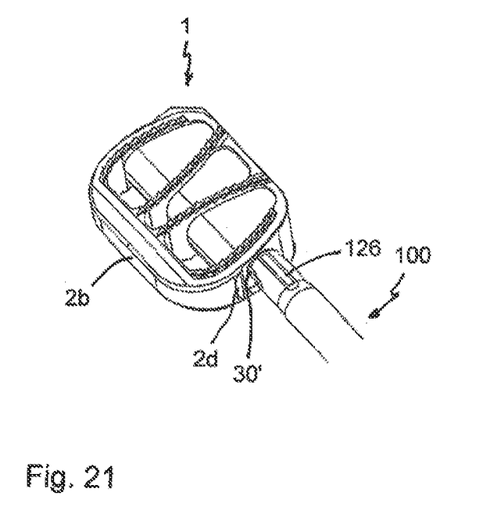
FIG. 21 shows a perspective view of the intervertebral implant with the insertion device connected to a still further receiving portion.
Figure 22:
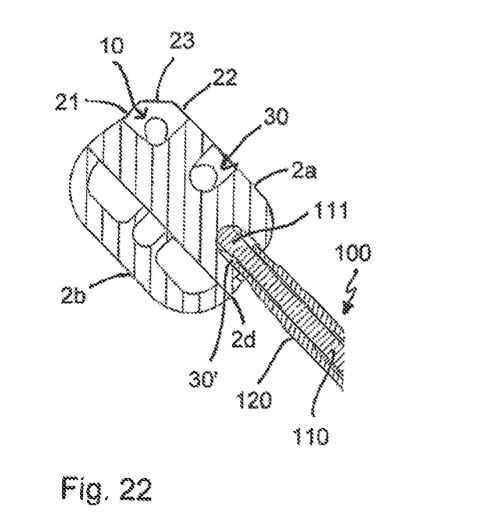
FIG. 22 shows a cross-sectional view of the intervertebral implant with the insertion device connected to the still further receiving portion as shown in FIG. 21.

FIGS. 19 and 20 show the engagement of the intervertebral implant through the additional recess 30 in the front wall 2a. FIGS. 21 and 22 show the engagement of the intervertebral implant through the additional recess 30' in the in the left sidewall 2d. In these configurations, the implant and the insertion device can be locked together in a single position.

Generally, in use, when the engagement portion 111 is in the 90° tilted upright position, the engagement portion is freely pivotable around the rotational axis R, so that a plurality of angular positions of the insertion device relative to the interval implant can be adjusted and achieved. When the drive shaft 110 is retracted with the engagement portion 111 being in the upright position, the engagement portion presses from inside against a wall of the recess 10 so that the insertion device and the implant are pulled together. Thereby, various angular positions can be fixed. With the abutment surfaces, predefined angular positions, such as 0°, 90°, or 45° as shown in the exemplary embodiment, can be fixed in a form-fit manner. Intermediate angular positions may also be achieved by the aid of the guiding surfaces and a force-fit connection. Loosening the fixation allows adjustments to the relative position between intervertebral implant and the insertion device without disconnecting the insertion device from the implant. This may be particularly useful for a lateral or anterior approach to the intervertebral space. The insertion device can be disconnected from the intervertebral implant by tilting the engagement portion 111 by 90° and removing or detaching the engagement portion through the opening 11.

By means of the aforementioned steps, various access paths to an intervertebral space can be realized. Only by way of example, in a surgical TLIF method, a small incision is made near the center of the back of a patient. Access is made to the damaged disk, the disk is removed, and the intervertebral implant filled with bone graft is inserted. The spinal segment is then stabilized, for example, using pedicle screw and rods. The intervertebral implant and the insertion device according to embodiments of the invention open a variety of possibilities to engage the intervertebral implant and to insert the intervertebral implant into the intervertebral space. Once the intervertebral implant is finally implanted in the intervertebral space, the drive shaft is pushed forward again, tilted by 90°, and removed from the recess 10 or one of the recesses 30, 30', respectively.

Figure 23:
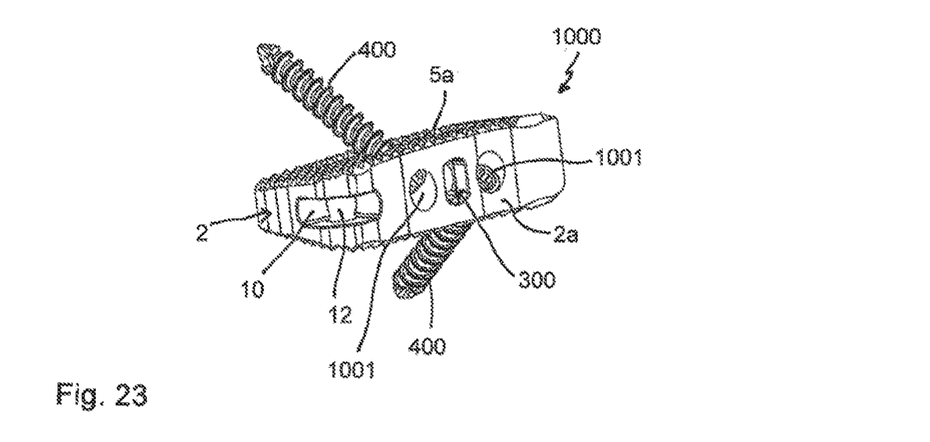
FIG. 23 shows a perspective view of a further modified embodiment of the intervertebral implant that is formed as an ALIF intervertebral implant.
Figure 24:
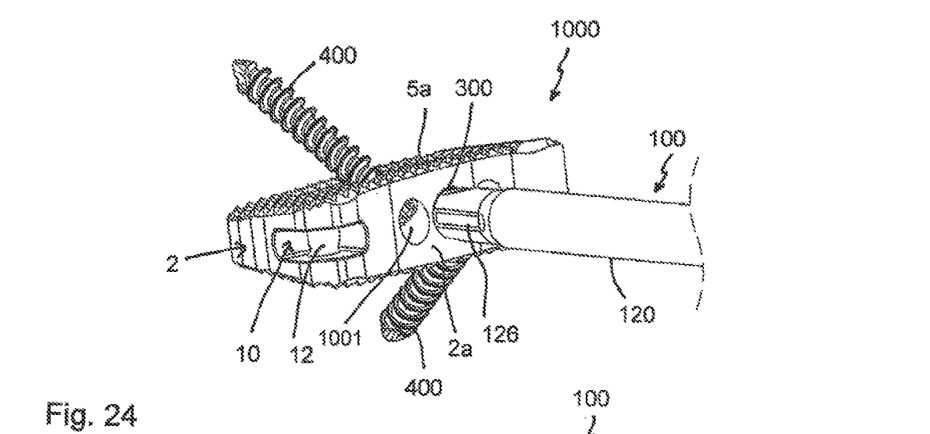
FIG. 24 shows a perspective view of the intervertebral implant of FIG. 23 with the insertion device connected thereto.
Figure 25:
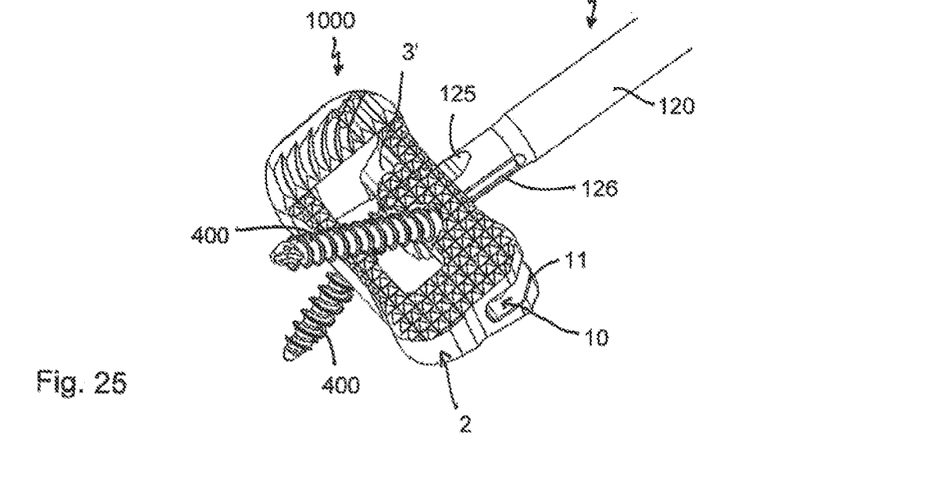
FIG. 25 shows a perspective view from a top of the intervertebral implant and the connected insertion device as shown in FIG. 24.

Turning now to FIGS. 23 to 25 a modified embodiment of the intervertebral implant is shown. The intervertebral implant 1000 is an ALIF intervertebral implant that has a slightly modified inner structure, specifically with respect to the solid body 3', the top face 5a, and the bottom face 5b. In addition, holes 1001 are provided that are configured to receive screws 400 for engaging the adjacent upper and lower vertebral bodies, respectively. The intervertebral implant 1000 also has the recess 10 with the elongate opening 11 as in the previous embodiment. The recess 10 may be provided at another side of the sidewall 2. An additional recess 300 in the middle of the front wall 2a forms an alternate receiving portion for the insertion device. The recess 300 is rotated by 90° compared to the recess 30 of the previous embodiment. In greater detail, the additional recess 300 extends with the opposite long sides in a vertical direction. By means of this, the necessary space for the recess 300 in the lateral direction can be reduced. This provides space for the additional holes 1001 for the screws 400 to the left and to the right of the additional recess 300 on the front wall 2a.

Various other modifications of the implant and/or the insertion device may further be made without departing from the scope of the invention.

The intervertebral implant shown in the above-described embodiments is only an example. The contour and shape of the intervertebral implant may be different according to specific clinical requirements. For example, the contour may have any other shape, such as circular, rectangular, oval, kidney shaped, among others. In some embodiments, the height of the sidewall may be constant throughout the implant. The intervertebral implant may also be in the form of a three-dimensional network or grid structure that can be manufactured, for example, by 3D printing techniques. In a further modified embodiment, the intervertebral implant may be a dummy implant or testing implant that is used for a trial procedure.

The number, orientation, and/or sequence of the abutment surfaces for generating a form-fit connection between the implant and the insertion device, and the number and/or position of the guiding surfaces is not limited to those shown in the disclosed embodiments. Various other abutment surfaces may be provided for adjusting the connection between the intervertebral implant and the insertion device at various other angles. The guiding surfaces may also be omitted.

In some embodiments, the elongate opening can be at another position. Still further, the elongate opening may extend vertically or at an incline. In some embodiments, more than one elongate opening with a recess for pivoting the implant relative to the insertion device may be provided. Also, a number of additional recesses for receiving the insertion device can be more or less than that shown in the described embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An intervertebral implant comprising:
a body insertable into an intervertebral space, the body comprising a first face, a second face connected to and opposite the first face, and an axis of rotation extending from the first face to the second face, wherein the body defines a hollow space between the first and second faces configured to accommodate an engagement portion of an insertion device, and first, second, and third openings each formed between the first and second faces, wherein the first, second, and third openings are spaced apart from one another and are interchangeably connectable with the insertion device;
wherein the first opening opens into the hollow space and extends circumferentially around the axis of rotation from a first end to a second end that is angled relative to the first end when viewed in a cross-section perpendicular to the axis of rotation to facilitate pivoting of the intervertebral implant relative to the insertion device about the axis of rotation when the engagement portion of the insertion device is in the hollow space.

2. The intervertebral implant of claim 1, wherein the hollow space comprises a spherical portion.

3. The intervertebral implant of claim 2, wherein the axis of rotation extends through a center of the spherical portion of the hollow space and is substantially parallel to a sidewall that extends between the first and second faces.

4. The intervertebral implant of claim 1, wherein the intervertebral implant is pivotable by about 90° relative to the insertion device.

5. The intervertebral implant of claim 1, wherein a sidewall that extends between the first and second faces comprises two opposite long sides and two opposite short sides extending between the long sides, and wherein the first opening is formed at a transition between one of the long sides and one of the short sides.

6. The intervertebral implant of claim 5, wherein at least one of the second or third openings is formed on one of the long sides or on one of the short sides.

7. The intervertebral implant of claim 1, wherein at least one of the second or third openings is connectable with the insertion device in an unadjustable manner.

8. The intervertebral implant of claim 1, wherein the intervertebral implant is monolithic.

9. An intervertebral implant comprising:
a body insertable into an intervertebral space, the body comprising a first face, a second face connected to and opposite the first face, and an axis of rotation extending from the first face to the second face, wherein the body defines a hollow space between the first and second faces configured to accommodate an engagement portion of an insertion device, the hollow space being accessible from outside the body through an opening formed between the first and second faces;

wherein when viewed in a cross-section perpendicular to the axis of rotation, the intervertebral implant has an outer profile defining the opening that has a first abutment surface having a flat contour that engages the insertion device in a form-fit manner at a first angular position, a second abutment surface having a flat contour that engages the insertion device in a form-fit manner at a second angular position, and a curved contour that extends circumferentially around the axis of rotation between the first and second abutment surfaces to facilitate pivoting of the intervertebral implant relative to the insertion device at least partially between the first and second angular positions, the curved contour further being configured to engage the insertion device to hold the intervertebral implant at at least one angular position different from the first and second angular positions when the engagement portion of the insertion device is in the hollow space.

10. The intervertebral implant of claim 9, wherein the hollow space comprises a spherical portion.

11. The intervertebral implant of claim 10, wherein the axis of rotation extends through a center of the spherical portion of the hollow space and is substantially parallel to a sidewall that extends between the first and second faces.

12. The intervertebral implant of claim 9, wherein the first abutment surface and the second abutment surface each comprises a planar surface.

13. The intervertebral implant of claim 9, wherein at least one of the first abutment surface or the second abutment surface is formed at a sidewall that extends between the first and second faces.

14. The intervertebral implant of claim 9, wherein the first and second angular positions are arranged at about 90° relative to each other.

15. The intervertebral implant of claim 9, further comprising a third abutment surface having a flat contour that engages the insertion device in a form-fit manner at a third angular position different from the first and second angular positions.

16. The intervertebral implant of claim 9, wherein the curved contour of the opening forms a guiding surface configured to cooperate with a corresponding guiding surface of the insertion device to facilitate pivoting of the intervertebral implant relative to the insertion device.

17. The intervertebral implant of claim 16, wherein the guiding surface of the intervertebral implant is cylindrical.

18. A system comprising:
an intervertebral implant comprising a body insertable into an intervertebral space, the body comprising a first face, a second face connected to and opposite the first face, and an axis of rotation extending from the first face to the second face, wherein the body defines a hollow space between the first and second faces, a first opening formed between the first and second faces that opens into the hollow space, and a second opening formed between the first and second faces that is spaced apart from the first opening and that is shaped differently from the first opening; and
an insertion device comprising an engagement portion formed at an end of a drive shaft for connecting to the intervertebral implant;
wherein when the engagement portion of the insertion device is in the hollow space of the intervertebral implant, the first opening is configured to facilitate pivoting of the intervertebral implant relative to the insertion device about the axis of rotation; and
wherein the engagement portion of the insertion device is further insertable through the second opening to connect the insertion device to the intervertebral implant.

19. The system of claim 18, wherein the insertion device further comprises a guiding sleeve configured to movably hold the drive shaft, the guiding sleeve comprising an abutment surface configured to abut against the intervertebral implant.

20. The system of claim 19, wherein when the engagement portion of the insertion device is in the hollow space of the intervertebral implant, the guiding sleeve is configured to be tightened against the intervertebral implant to fix an angular position of the insertion device relative to the intervertebral implant.

21. The system of claim 18, wherein the engagement portion has a spherical portion corresponding to a spherical shape of the hollow space of the intervertebral implant.

22. The system of claim 18, wherein the second opening is connectable with the insertion device in an unadjustable manner.

* * * * *

UNITED STATES PATENT AND TRADEMARK OFFICE
CERTIFICATE OF CORRECTION

| | | |
|---|---|---|
| PATENT NO. | : 12,343,264 B2 | Page 1 of 1 |
| APPLICATION NO. | : 17/536824 | |
| DATED | : July 1, 2025 | |
| INVENTOR(S) | : Timo Biedermann | |

It is certified that error appears in the above-identified patent and that said Letters Patent is hereby corrected as shown below:

On the Title Page

Item (54), in Column 1, under "Title", Line 1, delete "INTER VERTEBRAL" and insert -- INTERVERTEBRAL --.

In the Drawings

Sheet 1 of 10, Fig 1, Line 10, delete "30" and insert -- 30′ --.

In the Specification

On Column 1, Line 1, delete "INTER VERTEBRAL" and insert -- INTERVERTEBRAL --.

On Column 7, Lines 11-19, delete "The positioning flat surfaces 125 indicate the position of the cylindrical projections 122, and may serve for orienting the insertion device correctly during connection with the intervertebral implant. Moreover, at least one longitudinally extending positioning mark 126 at an outside of the front portion of the guiding sleeve 120 may further be provided that is 90° offset from the positioning flat surfaces 125 and that indicates the position of the cylindrical guiding surface 124." and insert the same on Column 7, Line 10, as a continuation of the same paragraph.

Signed and Sealed this
Sixteenth Day of December, 2025

John A. Squires
*Director of the United States Patent and Trademark Office*